United States Patent
Passerini et al.

(10) Patent No.: US 10,296,707 B2
(45) Date of Patent: May 21, 2019

(54) SYSTEM AND METHOD FOR PATIENT-SPECIFIC IMAGE-BASED GUIDANCE OF CARDIAC ARRHYTHMIA THERAPIES

(71) Applicant: Siemens Healthcare GmbH, Erlangen (DE)

(72) Inventors: Tiziano Passerini, Plainsboro, NJ (US); Tommaso Mansi, Plainsboro, NJ (US); Ali Kamen, Skillman, NJ (US); Bogdan Georgescu, Plainsboro, NJ (US); Dorin Comaniciu, Princeton Junction, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 777 days.

(21) Appl. No.: 14/683,245

(22) Filed: Apr. 10, 2015

(65) Prior Publication Data
US 2015/0294082 A1 Oct. 15, 2015

Related U.S. Application Data

(60) Provisional application No. 61/977,739, filed on Apr. 10, 2014.

(51) Int. Cl.
*G01N 33/48* (2006.01)
*G01N 33/50* (2006.01)
*G06F 19/00* (2018.01)
*G16H 50/50* (2018.01)
*A61N 1/362* (2006.01)

(52) U.S. Cl.
CPC ............ *G06F 19/00* (2013.01); *G16H 50/50* (2018.01); *A61N 1/3621* (2013.01)

(58) Field of Classification Search
None
See application file for complete search history.

(56) References Cited

U.S. PATENT DOCUMENTS

| | | |
|---|---|---|
| 7,668,354 B2 | 2/2010 | O'Donnell et al. |
| 7,916,919 B2 | 3/2011 | Zheng et al. |
| 2010/0040272 A1 | 2/2010 | Zheng et al. |
| 2012/0022843 A1 | 1/2012 | Ionasec et al. |
| 2013/0197881 A1 | 8/2013 | Mansi et al. |
| 2013/0216110 A1 | 8/2013 | Zheng et al. |
| 2013/0226542 A1 | 8/2013 | Rapaka et al. |
| 2014/0088943 A1 | 3/2014 | Trayanova et al. |
| 2014/0122048 A1 | 5/2014 | Vadakkumpadan et al. |
| 2015/0042646 A1 | 2/2015 | Comaniciu et al. |

FOREIGN PATENT DOCUMENTS

| | | |
|---|---|---|
| WO | WO 2012/109618 A2 * | 8/2012 |
| WO | WO 2013/109390 A1 * | 7/2013 |
| WO | WO2014133924 A1 | 9/2014 |

OTHER PUBLICATIONS

Wu et al. Robust tracking of a virtual electrode on a coronary sinus catheter for atrial fibrillation ablation procedures. Proceedings of SPIE, vol. 8316, pp. 83162U1 to 83162U-8. (Year: 2012).*
Mansi T. et al. Virtual Pulmonary Valve Replacement Interventions with a Personalised Cardiac Electromechanical Model. pp. 75-90 in: Magnenat-Thalmann N., Zhang J., Feng D. (eds) Recent Advances in the 3D Physiological Human. Springer, London (Year: 2009).*
Sermnesant et al. Toward patient-specific myocardial models of the heart. Heart Failure Clin. vol. 4, pp. 289-301. (Year: 2008).*
Peyrat et al., "A Computational Framework for the Statistical Analysis of Cardiac Diffusion Tensors: Application to a Small Database of Canine Hearts,", IEEE TMI, 26(11): 1500-1514, 2007.
Rapaka, et al., "LBM-EP: Lattice-boltzmann method for fast cardiac electrophysiology simulation from 3d images", In: Medical Image Computing and Computer-Assisted Intervention MICCAI, 2012, pp. 33-40, vol. 7511, Springer Berlin Heidelberg.

* cited by examiner

*Primary Examiner* — Russell S Negin

(57) ABSTRACT

A method and system for image-based patient-specific guidance of cardiac arrhythmia therapies is disclosed. A patient-specific anatomical heart model is generated from medical image data of a patient. A patient-specific cardiac electrophysiology model is generated based on the patient-specific anatomical heart model and electrophysiology measurements of the patient. One or more virtual electrophysiological interventions are performed using the patient-specific cardiac electrophysiology model. One or more pacing targets or ablation targets based on the one or more virtual electrophysiological interventions are displayed.

70 Claims, 4 Drawing Sheets

200   210

Cardiac electrophysiology
302

Torso potential
304

ECG signal
306

SYSTEM AND METHOD FOR PATIENT-SPECIFIC IMAGE-BASED GUIDANCE OF CARDIAC ARRHYTHMIA THERAPIES

This application claims the benefit of U.S. Provisional Application No. 61/977,739, filed Apr. 10, 2014, the disclosure of which is herein incorporated by reference in its entirety.

BACKGROUND OF THE INVENTION

The present invention relates to medical image-based guidance of cardiac arrhythmia therapies, and more particularly to guidance of electrophysiological interventions using interventional medical images and a personalized computational cardiac electrophysiology model.

Ablation procedures for cardiac arrhythmias have proven to be successful for a large variety of cardiac electrophysiology troubles. Atrial fibrillation (Afib), ventricular tachycardia (VT), and ventricular fibrillation (VF), for example, can be treated, or at least controlled, in several classes of patients. The general idea behind ablation therapy is to destroy the cells that trigger the arrhythmias. These cells can be ectopic, i.e., they trigger uncontrolled electrical signals spontaneously, or exits points of slow conducting pathways that can be found, for example, around or within myocardium scars. The success of the ablation therapy relies on the ability of the electrophysiologist to identify the arrhythmogenic regions. While Afib ablation has become systematic in most patients, finding the regions to ablate in post myocardium infarction (MI) patients is extremely challenging due to the variability in scar geometry and local tissue substrate. Current practice is still lacking of a systematic clinical strategy, which may explain the rather unsatisfactory success rate of ablation therapies for VT (from 50% to 90%).

BRIEF SUMMARY OF THE INVENTION

The present invention provides a method and system for image-based patient-specific planning or guidance of cardiac arrhythmia therapies. Embodiments of the present invention guide cardiac electrophysiology (EP) interventions using interventional images and a personalized computational cardiac EP model. Embodiments of the present invention perform virtual pacing of the heart to test different configurations of a therapy, such as cardiac resynchronization therapy (CRT), and perform virtual ablation to assess the efficacy of an ablation strategy, such as for ventricular tachycardia (VT) or Atrial fibrillation (Afib) ablation, in order to reduce the intervention duration while maximizing the outcome of the therapy for the patient. Embodiments of the present invention can be performed in real-time or near real-time to provide model-based guidance during an intervention procedure or can be performed off-line as a planning tool.

In one embodiment of the present invention, a patient-specific anatomical heart model is generated from medical image data of a patient. A patient-specific cardiac electrophysiology model is generated based on the patient-specific anatomical heart model and electrophysiology measurements of the patient. One or more virtual electrophysiological interventions are performed using the patient-specific cardiac electrophysiology model. One or more pacing targets or ablation targets based on the one or more virtual electrophysiological interventions are displayed.

These and other advantages of the invention will be apparent to those of ordinary skill in the art by reference to the following detailed description and the accompanying drawings.

DETAILED DESCRIPTION

The present invention relates to patient-specific planning and guidance of cardiac arrhythmia therapies using medical imaging data. Embodiments of the present invention are described herein to give a visual understanding of the methods for patient-specific guidance of cardiac arrhythmia therapies using medical imaging data. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Embodiments of the present invention guide cardiac electrophysiology (EP) interventions using interventional images and a personalized computational cardiac EP model. Embodiments of the present invention perform virtual pacing of the heart to test different configurations of a therapy, such as cardiac resynchronization therapy (CRT), and perform virtual ablation to assess the efficacy of an ablation strategy, such as for ventricular tachycardia (VT) or Atrial fibrillation (Afib) ablation, in order to reduce the intervention duration while maximizing the outcome of the duration for the patient. Embodiments of the present invention can be performed in real-time or near real-time to provide model-based guidance during an intervention procedure or can be performed off-line as a planning tool. As such, embodiments of the present invention can be viewed as a "GPS" system for ablation therapy of cardiac arrhythmias.

In various embodiments of the present invention, interventional imaging, advanced image analytics, and a fast electrophysiology model can be combined while leveraging massively parallel hardware architectures. Anatomical model and tissue quantification can be realized during an intervention, before starting an electrophysiology study. A patient-specific electrophysiology model can be estimated from a first electrophysiology study at spontaneous rhythm and, if available, torso potential measurements of the patient. Next, the patient-specific electrophysiology model can be used to identify pacing sites and ablation target candidates. During the intervention, the patient-specific electrophysiology model is updated based on new measurements. Fast image analytics can also be coupled with image-based anatomical electrophysiology mapping registration techniques to monitor ablations while updating the electrophysiology information in the patient-specific electrophysiology model.

Figure 1:
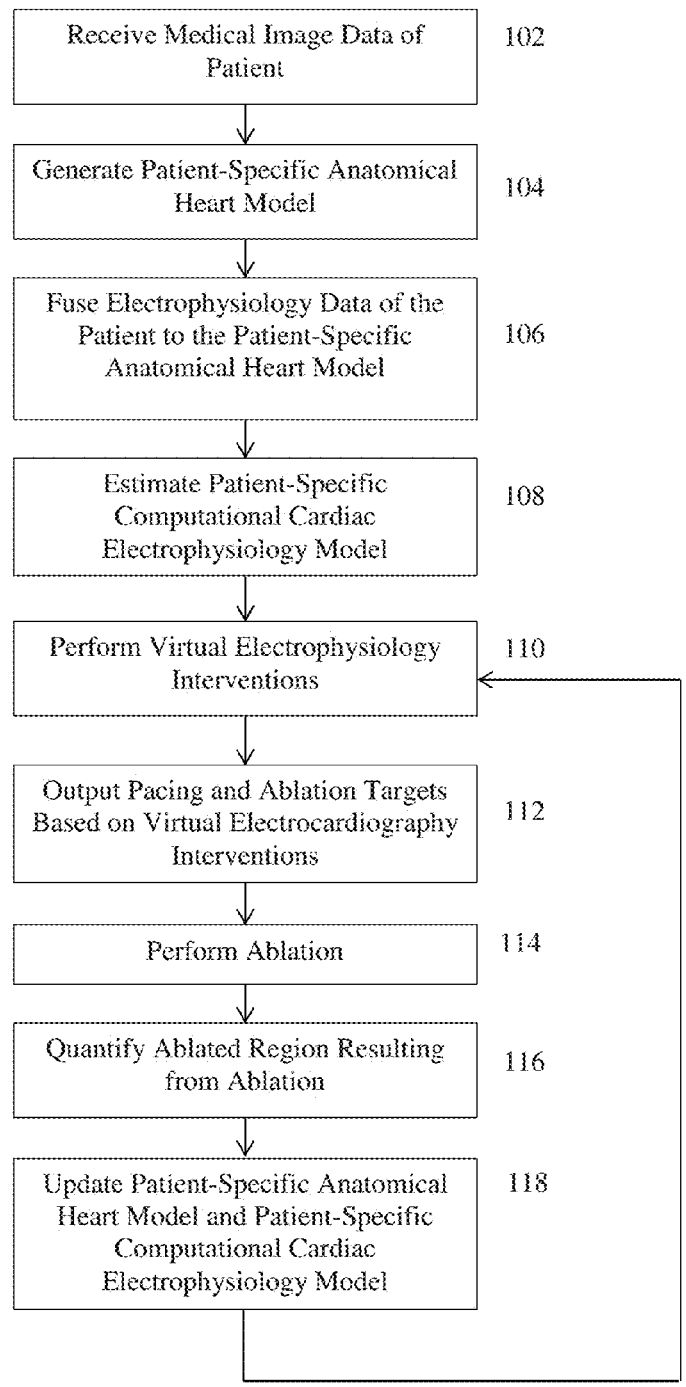
FIG. 1 illustrates a method for patient-specific guidance of a cardiac electrophysiology intervention according to an embodiment of the present invention.

FIG. 1 illustrates a method for patient-specific guidance of a cardiac electrophysiology intervention according to an embodiment of the present invention. The method of FIG. 1 describes patient-specific guidance of an ablation therapy intervention, but the present invention is not limited thereto and the method of FIG. 1 may be similarly applied to other cardiac electrophysiology interventions, such as CRT, as well. In an advantageous implementation, the method steps of FIG. 1 can be performed in real-time or near real-time during the electrophysiology intervention. However, various method steps of FIG. 1, such as steps 102-112, may be performed offline in advance of the electrophysiological intervention in order to plan the electrophysiological intervention. While the method of FIG. 1 can be implemented offline for planning the electrophysiological intervention and can be implemented using various modalities of medical imaging data, in an advantageous implementation the method of FIG. 1 can be performed during the electrophysiological intervention using an interventional magnetic resonance imaging (MRI) system, which is a unique environment that enables live imaging of cardiac anatomy and catheters during an intervention.

At step 102, medical image data of the patient is received. The medical image data can be acquired using any type of medical imaging modality, such as magnetic resonance imaging (MRI), computed tomography (CT), three-dimensional rotational angiography, ultrasound (US), etc., provided that the heart is visible in the medical image data. In an advantageous implementation, the medical image data includes three dimensional (3D) and/or 4D (3D+time) medical image data. The medical image data can be received directly from an image acquisition device, such as an MRI scanner, a CT scanner, a C-arm image-acquisition device, or an US scanner, or the medical image data can be received by loading previously stored medical image data of the patient. In an advantageous embodiment, the medical image data can include 3D or 4D interventional (intraoperative) images (e.g., cine MRI or delayed enhanced MRI (DE-MRI)) that is acquired at the beginning of the electrophysiological intervention and received in real-time or near real-time from the medical image acquisition device. However, it is also possible that the medical image data can be pre-operative cardiac image data acquired prior to the electrophysiological intervention.

At step 104, a patient-specific anatomical heart model is generated from the medical image data of the patient. The patient-specific anatomical heart model can be generated by extracting a patient-specific heart morphology model from the medical image data, segmenting scars and border zones, and estimating a myocardial fiber model. However, the accurate segmentation of cardiac chambers, scars, and border zones from MR images can be challenging and often requires manual intervention, and many standard segmentation approaches are not suitable for use in the operating room during an intervention procedure. Embodiments of the present invention can automatically estimate geometry of the heart chambers from interventional MR images using machine learning algorithms based on a Marginal Space Learning (MSL) framework, as described in greater detail below.

The patient-specific heart morphology model can be a comprehensive geometrical model that represents the patient-specific heart morphology. In an advantageous embodiment, the patient-specific heart morphology model includes individual anatomical models representing the morphology of various heart components. The models are highly modular and can be customized depending on the application. The complete heart model can comprise the left ventricle (LV), left atrium (LA), left outflow tract, aortic root, pulmonary veins, right ventricle (RV), right atrium (RA), right outflow tract, RV neck, and veins. Each of these components can be used individually or jointly according to data availability and clinical application. In an exemplary embodiment, the LV and RV anatomical models estimated from the pre-operative cardiac image data are used. In a possible implementation, for example for guiding CRT or ablation therapy to treat VT or VF, only the LV and RV are explicitly modeled. In other possible implementations, for example for guiding ablation therapy to treat Afib, a model for either the LA or RA can be extracted in addition to LV and RV or all of the heart chambers can be extracted. It is also possible that the comprehensive model including all of the heart components is extracted. The modularity of this framework enables the use of images in which only part of the anatomy is visible.

The anatomical model for each heart component can be extracted individually. In particular, for each heart chamber, the heart chamber segmentation can be formulated as a two-step learning problem: anatomical structure localization and boundary delineation. In an advantageous embodiment, marginal space learning (MSL) can be used to apply machine learning to 3D object detection. The idea of MSL is not to learn a monolithic classifier directly in the full similarity transformation parameter space but to incrementally learn classifiers on marginal spaces. In particular, the detection of each heart chamber can be split into three problems: position estimation, position-orientation estimation, and position-orientation-scale estimation. A separate classifier is trained based on annotated training data for each of these estimation problems. Each classifier can be a probabilistic boosting tree (PBT) classifier trained based on annotated training data. The classifiers in the lower dimensional marginal spaces are used to prune the searching space efficiently. This object localization stage results in an estimated transformation (position, orientation, and scale) of the object (e.g., heart chamber). After automatic object localization, the mean shape model of the object is aligned with the estimated transformation to get a rough estimate of the object shape. The shape is then deformed locally to fit the object boundary. Active shape models (ASM) can be used to deform an initial estimate of a non-rigid shape under the guidance of the image evidence and the shape prior. However, a non-learning based generic boundary detector, as used in conventional ASM applications, does not work effectively in heart chamber deformation due to the complex background and weak edges. Instead, a learning based boundary detector can be used to exploit more image evidences to achieve a robust boundary detection. Additional details regarding MSL-based heart chamber segmentation are described in U.S. Pat. No. 7,916,919, issued Mar. 29, 2011, and entitled "System and Method for Segmenting Chambers of a Heart in a Three Dimensional Image", United States Published Patent Application No. 2010/0040272, and United States Published Patent Application No. 2012/0022843, which are incorporated herein by reference.

Once the individual anatomical models for the various heart components are extracted from the medical image data, the patient-specific heart morphology model is fused into a single volumetric mesh representation and surface elements of the mesh are tagged into surface zones. For example, in the case of VT/VF ablation therapy, the patient-specific LV and RV anatomical models can be fused into a single anatomical model of the bi-ventricular myocardium. In particular, the extracted LV and RV anatomies are fused into a single volumetric mesh representation. Vertices of this volumetric mesh are tagged into surface zones (LV endocardium, LV septum, RV endocardium, RV septum) according to the underlying anatomy of the estimated surface models. According to an advantageous embodiment, tetrahedral elements can be used to accurately represent the details of the bi-ventricular anatomy. In cases in which one or both atria are also extracted (e.g., Afib ablation therapy), the models for all of the extracted heart chambers are fused into a single volumetric mesh representation.

Scar tissue and border zone tissue can be segmented using DE-MRI image data. The 3D model of the heart chambers can be rigidly registered on a DE-MRI image using the coordinates of the MR scanner plus correlations between image information in the DE-MRI image and the 3D heart model. An expectation-minimization algorithm with belief prior and spatial regularization can then be employed to segment the scar and border zone tissue. This method works on in-vivo, multi-modality images and adds smoothing constraints for increased robustness to noise. First, the myocardium is extracted from the DE-MRI image using the registered 3D model. Healthy tissue and scar tissue are modeled using a Gaussian mixture model with two modes. Given a three-class segmentation, the parameters of the mixture model are estimated, from which a belief value $\lambda$ is derived. Voxels with $\lambda<0.5$ are rejected from the model and classified as border zone. The border zone is a zone surrounding the scar tissue that represents healing tissue. For increased robustness and regularity, Markov random fields are employed to reject voxels according to the state of neighboring voxels. Furthermore, voxels farther than N-mm from the current scar estimate are never rejected, assuming that border zone can only be found in the proximity of scars. A graph-cut algorithm is also employed to estimate smooth interfaces between tissue types. The graph-cut algorithm is initialized with a coarse classification obtained using a k-means algorithm or similar algorithm and is iterated until convergence (e.g., when the parameters of the mixture model do not change anymore). The segmented scar tissue and surrounding border zone is then mapped to the volumetric mesh representation of the heart chambers.

A model of myocardium fiber architecture is then generated based on the patient's heart geometry. In one embodiment, the 3D anatomical model of the heart, including the scar and border zone information are rasterized on an isotropic grid for subsequent electrophysiology computation and a dense fiber map is estimated on that grid to cope with tissue anisotropy. The fiber model may be computed directly from the anatomical model using a rule-based method. A generic model of myocardium fiber architecture that includes fiber and fiber sheets is computed. For the ventricles, a rule-based strategy is followed to generate the fiber architecture to cover the entire bi-ventricular myocardium from apex to valves. Below the basal plane, which is identified automatically using point correspondences of the initial triangulations of the anatomical model, the fiber elevation angle $\alpha$, i.e. their angle with respect to the short axis plane, varies linearly across the myocardium, e.g., from −70 on the epicardium to +70 on the endocardium (values that can be defined by the user). Similarly, the sheet direction, which is defined by the angle $\beta$ with respect to the outward transmural axis, varies transmurally, e.g., from +45 on the epicardium to −45 on the endocardium (values that can be defined by the user). $\alpha$ and $\beta$ are computed for each point of the volumetric bi-ventricular myocardium mesh between the apex and basal plane based on the geodesic distance to the endocardia and epicardia identified by the facet tags: $\alpha=(d_{epi}\alpha_{endo}+d_{endo}\alpha_{epi})/(d_{endo}+d_{epi})$ where $d_{epi}$, $d_{endo}$, $\alpha_{epi}$, and $\alpha_{endo}$ are the distances and angles at the endocardium and epicardium, respectively. The fiber and sheet orientations are then fixed around each valve. In particular, fibers are longitudinal around the aortic valve and tangential around the mitral, tricuspid, and pulmonary valves, and sheet normals are oriented towards the barycenter of the valves. The local orthonormal basis is then interpolated from the basal plane to the apex, first by following the myocardium surface, then throughout the myocardium thickness. For orthonormality preservation, the interpolation can be performed using a Log-Euclidean framework. A similar rule-based fiber model can be applied to the atria based on histological studies.

In another embodiment, if in-vivo diffusion tensor (DT) MR images are available, DT MR images of the patient's cardiac fibers can be directly mapped to the anatomical model through image registration. In this case, the DT MR image is non-linearly registered to the medical image in which the LV and RV models are detected. The resulting transformation is used to deform the tensor field in the DT MR image towards the anatomical model. The Finite Strain method, the details of which are described in Peyrat et al., "A Computational Framework for the Statistical Analysis of Cardiac Diffusion Tensors: Application to a Small Database of Canine Hearts", IEEE TMI, 26(11):1500-1514, 2007, which is incorporated herein by reference, is used to reorient the tensors once the tensors are registered to the anatomical model. It is also possible, that an atlas of fiber architecture is available and the atlas is registered to the patient-specific anatomical model using standard image registration techniques.

Figure 2:
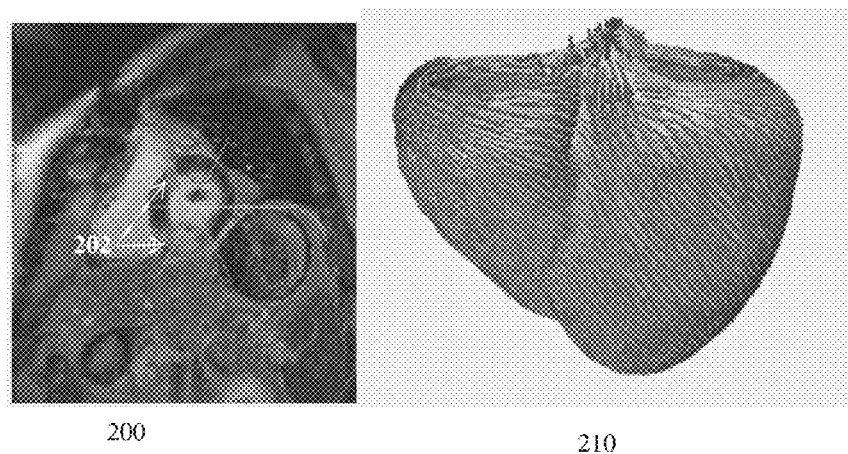
FIG. 2 illustrates exemplary results for scar tissue segmentation and a mapping of myocardial fibers on a patient-specific anatomical heart model.

FIG. 2 illustrates exemplary results for scar tissue segmentation and mapping myocardial fibers on a patient-specific anatomical heart model. As shown in FIG. 2, image 200 shows scar tissue 202 segmented from a DE-MRI image, and image 210 shows a patient-specific anatomical model of the LV and RV mapped with myocardial fibers.

Returning to FIG. 1, at step 106, electrophysiology (EP) data of the patient is fused with the patient-specific anatomical heart model. The EP data of the patient can include invasive cardiac EP maps acquired for the patient and/or body surface potential measurements. Body surface potential measurements are measurements of electrical potentials on the torso of the patient and can refer to body surface potential maps acquired using body surface mapping (BSM) or ECG measurements of the patient using ECG leads on a patient's torso (e.g., 12 lead ECG measurements). Invasive cardiac maps are generated invasively by measuring potentials at various points in the heart over time, for example using a catheter mapping system or a catheter basket system. In order to personalize a computational EP model using invasive cardiac EP maps, the cardiac EP data must be registered to the patient-specific anatomical heart model. In existing techniques for registering EP measurements to cardiac anatomy, the registration is slow and relies on pre-operative data that can be obsolete at the time of the intervention. According to an embodiment of the present invention, the interventional setup performs on-line registration of invasive cardiac EP maps and the patient-specific anatomical model during the intervention procedure. This registration is described herein for cardiac EP maps acquired using a catheter mapping system and for cardiac EP maps acquired using a catheter basket system.

Catheter mapping systems require probing the heart at different locations with a probe that measures the local ECG, from which EP parameters are derived. This approach is accurate, but measurements are performed over several heartbeats, which makes the mapping difficult during arrhythmias. In an advantageous embodiment of the present invention, N landmark points are probed by the catheter. While keeping the catheter anchored at each of the N points, a fast 3D MRI acquisition is performed, resulting in N 3D MRI images. The image quality does not need to be high, only the catheter and the endocardial interfaces need to be visible. Each of the N 3D images is then rigidly registered to the image from which the patient-specific anatomical heart model was extracted (e.g., DE-MRI image) using cross-correlation to cope with the noise in each of the 3D images, and the N transformations resulting from registering the N 3D images to the anatomical DE-MRI are averaged using Log-Euclidean framework resulting in the transformation matrix P. The positions of the catheter are detected in the 3D MRI images, for example using a machine learning algorithm, and a transformation M is estimated between the catheter coordinate system and the MRI coordinate system. The final transformation T=PM is used to map the catheter points to the patient-specific anatomical heart model and all subsequent EP measurements are also registered to the patient-specific anatomical heart model using the final transformation T. Although the calibration procedure takes N fast MRI scans, subsequent electrophysiology measurements are mapped in real-time to the cardiac anatomy, as only a matrix-vector multiplication is required for each measurement. In this way, new EP measurements can be integrated with the patient-specific anatomical model in real-time as they are acquired during the intervention procedure. It can be noted that, in addition to the on-line processing described above, this method can be similarly applied to off-line processing provided that the required EP data and image data is stored. In a possible implementation, the transformation matrix can be complemented by a non-linear motion model of cardiac contraction for increased accuracy. In this case, the motion model can be learned from dynamic segmentation of the heart in multiple frames of a cine MRI sequence acquired at the beginning of the intervention.

Contrary to contact mapping systems, basket catheters measure the EP activity over a basket that is deployed in the heart chamber. Far-field theory is employed to process the received electrical activity. While one-beat measurements can be acquired, which are advantageous for arrhythmia mapping, the precise location of the measured potential on the anatomy is not available. According to an embodiment of the present invention, the interventional MRI setup can be leveraged to register such EP measurements. Once the catheter basket is anchored inside the chamber, a fast 3D image (e.g., fast 3D MRI image) is acquired and rigidly or possibly non-linearly registered to the image (e.g., DE-MRI image) from which the anatomical model was derived. Using the estimated transformation, the basket is registered to the anatomical model. A model of far-field theory can then be used to map the EP measurements acquired by the basket to the 3D patient-specific anatomical heart model. Alternatively, simple Laplacian stream-lines can be used to map the EP measurements acquired by the basket to the patient-specific anatomical heart model.

In order to fuse body surface potential measurements (e.g., body surface potential maps acquired using BSM or ECG measurements) to the patient-specific anatomical heart model, the body surface measurements are mapped to a patient-specific torso model that is registered to the patient-specific anatomical heart model. A 3D image of the patient's torso can be acquired, for example at the beginning of the intervention, and a triangulated mesh of the patient's torso can be segmented from the 3D image using a segmentation algorithm, such as graph cuts. In a case in which 3D torso images cannot be acquired, 2D MRI scout images can used to generate a torso model. In this case, contours of the visible torso in the 2D scout images can be automatically extracted, for example using graph-cuts. A stored 3D torso atlas can then be registered based on the 2D scout images using an affine transformation to match the torso contours extracted from the 2D scout images. This registration algorithm leverages the scout image positions (axial, sagittal and coronal) for increased robustness and minimizes risks of local minima. Once the torso is modeled, the patient-specific torso model can be automatically registered to the heart model using the scanner coordinates. Lead positions from which the body surface potentials were measured are mapped to the torso model. For example the lead positions can be mapped automatically or using user-defined landmarks. The body surface potential measurements can then be back-projected to the patient-specific anatomical heart model.

Once the patient-specific torso model is registered to the patient-specific anatomical heart model, an electrical model of diffusion in the torso can be used to describe the coupling relationship between the heart and the torso. Electrical potentials on the torso can be calculated from cardiac potentials by first inferring extra-cellular potentials from transmembrane potentials on the epicardium, and then solving a Poisson equation using the boundary element method (BEM). The electrical coupling between the heart mesh and the torso mesh can be modeled by the linear relationship $\forall t$, $Y_t=T*X_t$, where $X_t(x)$ denotes the extra-cellular potentials on the epicardium, $Y_t(x)$ denotes the torso potentials, and T is the coupling matrix obtained by boundary element discretization of the heart-torso geometry and solving the Poisson equation for electrical potentials.

At step 108, a patient-specific computational cardiac EP model is estimated. The patient-specific computational cardiac EP model is a computational model of cardiac electrophysiology, which is personalized by estimating patient-specific parameters of the cardiac EP model representing tissue properties of the cardiac tissue based on the measured EP data of the patient. The patient-specific computational cardiac EP model computes cardiac electrophysiology and, once personalized, can be used to perform virtual electrophysiological interventions, for example to guide an electrophysiologist towards an optimal pacing site and identify an optimal ablation target. To that end, in an advantageous implementation, the cardiac EP model is fast enough to be personalized and executed on-line during the clinical intervention, while also being accurate enough to capture the complex pathological patterns observed in VT and Afib.

Computational EP models are typically calculated using finite element methods. However, finite element methods cannot be easily adapted to highly parallel architectures and do not scale well. According to an advantageous implementation, embodiments of the present invention utilize a Lattice-Boltzmann method for electrophysiology (LBM-EP) to solve a cellular model, such as the Mitchell-Schaeffer (MS) pseudo-ionic cellular model, over the patient-specific cardiac geometry. In this method, a Cartesian grid domain for electrophysiology computations is calculated using the patient-specific anatomical heart model. A Cartesian grid, with uniform grid spacing or possibly with unequal and spatially varying spacing, is first generated in a bounding box surrounding the anatomical heart model. Grid spacing can be defined by the user or fixed in the system. A level-set representation is then calculated from the patient-specific anatomical heart model as follows. For every node x of the grid, the shortest distance to the anatomical model mesh is calculated, and assigned to that node. In an advantageous embodiment, nodes inside the myocardium are defined by positive distances, and nodes not inside the myocardium are defined by negative distances. The opposite convention can be utilized as well without any modification. Nodes at myocardium, endocardia, and epicardium are tagged as such, as well as other nodes pertaining to the cardiac conduction system. For ventricular arrhythmias, the nodes of the patient-specific anatomical model on the Cartesian grid corresponding to the ventricular septum (to mimic the His Bundle) and the endocardia (to mimic the Purkinje system) can be tagged. Similar tagging can be employed for atrial arrhythmias, starting from the sino-atrial nodes and nodes corresponding to other fast conduction systems (e.g. Bachmann bundles). Available scars and border zones are also reported in the domain through additional level-set information. Fiber orientation f(x) is mapped to each node using rasterization techniques or is recomputed from the mapped endocardial and epicardial zones directly. A diffusion coefficient c(x) and an action potential duration APDd (x) is assigned to every myocardial node x of the Cartesian grid. Cell model parameters can also be mapped spatially at each node.

The computational cardiac EP model calculates the transmembrane potential at each node within the myocardium using the Lattice-Boltzmann Method for Electrophysiology (LBM-EP). The cardiac electrophysiology model calculates the variation of the transmembrane potential v(x,t) over time according to the mono-domain equation:

$$\frac{dv(x, t)}{dt} = R(x, t) + \nabla \cdot c(x) D(x) \nabla v(x, t), \quad (1)$$

where R(x,t) is a reaction term describing the cellular mechanisms giving rise to the action potential, c(x) is the local diffusivity to be estimated from the patient-specific data, D(x) is the anisotropy (transverse isotropy) matrix defined by $(1-\rho)f(x)f(x)^T + \rho \text{Id}$, $\rho$ being the ratio between the cross-fiber diffusivity and the fiber diffusivity (typically $\rho = 0.11 – 0.25$). It is also possible to use orthotropic or fully anisotropic tensors D(x) for improved characterization of the fiber architecture.

The choice of the reaction term R(x,t) depends on the cellular model of cardiac electrophysiology that is used. The method disclosed herein is modular in that it can handle any standard cellular models, such as, but not limited to the MS model proposed in Mitchell et al., "A Two-Current Model for the Dynamics of Cardiac Membrane", *Bulletin of Mathematical Biology*, 65(5):767-793, 2003, or the model proposed in Ten Tusscher, et al., "Cell Model for Efficient Simulation of Wave Propagation in Human Ventricular Tissue Under Normal and Pathological Conditions", *Physics in Medicine and Biology*, 51, pp 6141, 2006. For the MS cellular model for instance, we have:

$$R(x, t) = \frac{h(x, t) v^2(x, t)(1 - v(x, t))}{\tau_{in}} - \frac{v(x, t)}{\tau_{out}} + J_{stim}(x). \quad (2)$$

In this equation, $J_{stim}(x)$ is an external stimulus current. In virtual interventions simulated for intervention guidance or planning, virtual pacing can be performed by adding $J_{stim}(x)$ at one or several spatial locations chosen by the user or chosen automatically by the system. It is also possible that the position of a pacing electrode can be tracked using an embedded tracking method (e.g., electromagnetic tracking, bi-plane image-based tracking, etc.) when the electrophysiologist is pacing the heart at a given location, and the position of the pacing electrode returned by the embedded tracking method can be used to add a stimulus current to the model through $J_{stim}(x)$ at the acquired position. The amount of current that is added to the model is obtained from the catheter manufacturer specifications for instance, or manually defined. In Equation (2), h(x,t) is a gating variable that controls the state of the ion channels according to the following ordinary differential equation:

$$\frac{dh(x, t)}{dt} = \begin{cases} \frac{1 - h(x, t)}{\tau_{open}} & \text{if } v(x, t) < v_{gate} \\ \frac{-h(x, t)}{\tau_{close}} & \text{otherwise} \end{cases}.$$

$v_{gate}$ is a potential threshold, and $T_{in}$, $T_{out}$, $T_{open}$ and $T_{close}$ are parameters controlling the shape of the action potential and the restitution curve. In a possible embodiment, electrical diffusivity c(x) and action potential duration APDd(x) parameters of the cardiac EP model are personalized. In the MS cellular model, APDd(x) is directly related to $T_{close}(x)$ according to the formula $APDd_{max}(x) = T_{close}(X) \ln(T_{out}/(4T_{in}))$. In an advantageous implementation, only c(x) and $T_{close}(x)$ are estimated and the other parameters are kept constant to their default (i.e. nominal) values. However, it is also possible to implement this method to estimate these additional parameters as well.

Equation (1) is solved using the Lattice-Boltzmann method for electrophysiology, referred to herein as LBM-EP. LBM-EP is a highly parallelizable algorithm to solve monodomain electrophysiology equations. The LBM-EP algorithm is described in greater detail in United States Published Patent Application No. 2013/0226542, entitled "Method and System for Fast Patient-Specific Cardiac Electrophysiology Simulations for Therapy Planning and Guidance", which is incorporated herein by reference in its entirety. Contrary to standard finite-element methods, LBM-EP does not explicitly solve the reaction-diffusion equation but rather computes the "movement" of particles on a Cartesian grid, from which the reaction-diffusion behavior emerges. The particles can move according to fixed directions (or connectivities), with a certain probability. The algorithm includes two node-wise steps: streaming, which makes the particle jump from one node to another; and collision, which takes care of mass preservation and boundary conditions. It can be mathematically shown that this simple algorithm reproduces dynamics of the reaction-diffusion equation. In order to compute the cardiac electrophysiology using LBM-EP, domain boundaries are represented as level-sets and tissue anisotropy is modeled. In sinus rhythm, the electrocardiography model can be computed with periodic stimulus at the septum to mimic the fast conducting His bundle.

Since the LBM-EP method is completely node-wise and the time-integration is explicit, the computations can be done locally and the method is therefore easily adapted to highly parallel architectures. In an advantageous embodiment, the method can be implemented on one or more general purpose graphics processing units (GPGPU), which enables near real-time and accurate cardiac electrophysiology computation during the intervention. In this embodiment, this method can be optimized to fully benefit from the computational power of GPGPUs. For example, adaptive computational block aggregation can be performed to balance between computational power and memory bandwidth. Adaptive time-stepping methods can also be implemented to take into account the current EP dynamics, in particular in sinus rhythm regions. For example, small time steps can be used when the fast front propagation is occurring, larger time steps can be used during the refractory period, and even larger time steps can be used during the depolarization state. Adaptive mesh refinement techniques can also be implemented to reduce the overall computational effort in the presence of thick-walled structures (e.g., ventricles) and thin-walled structures (e.g., atria). The model can be interfaced with model repositories for greater flexibility.

The cardiac EP model is coupled with a boundary element model of potential propagation in soft tissue in order to calculate an ECG resulting from the simulated cardiac electrophysiology. The cardiac EP model computes a transmembrane potential for each node of the patient-specific anatomical heart model on the computational domain at each time step. An extra-cellular potential $\Phi_e$ is calculated at each node of the computational domain based on the transmembrane potential v(x,t) using a closed-form expression ($\Omega$ defines the computational domain; $|\Omega|$ is the number of elements therein):

$$\phi_e(x, t) = \frac{\lambda}{1+\lambda} \frac{1}{|\Omega|} \int_\Omega [v(y, t) - v(x, t)] dy, \quad (3)$$

where $\lambda$ is a constant diffusion anisotropy ratio, $\lambda = D_i(x)/D_e(x)$, and $D_i$ and $D_e$ are intra- and extra-cellular diffusivity tensors, respectively. The extra-cellular potential $\phi_e$ is then mapped back to the epicardium surface mesh using tri-linear interpolation. The extra-cellular potentials are then projected onto the torso surface mesh using a boundary element method (BEM). The potential $\phi(x)$ at any point x of the thoracic domain (torso surface mesh) can be calculated as:

$$\phi(x) = \frac{1}{4\pi} \int_{S_B} \phi_b \frac{r \cdot n}{\|r\|^3} dS_B - \frac{1}{4\pi} \int_{S_H} \left[ \phi_e \frac{r \cdot n}{\|r\|^3} + \frac{\nabla \phi_e \cdot n}{\|r\|} \right] dS_H, \quad (4)$$

where r is the vector defined by x and the integration point n, while $S_B$ and $S_H$ are the torso and epicardium surfaces, respectively. The body surface potential at the torso, $\phi_b$, can be expressed as a function of the extra-cellular potential $\phi_e$, which allows the potential to be calculated at any point on the torso. As described above, the torso mesh can be segmented from the medical image data using machine learning algorithms. According to a possible implementation, the body surface potential $\phi_b$ can be calculated for each vertex on the torso mesh. In another possible implementation, the body surface potential $\phi_b$ may be calculated only for vertices on the torso mesh corresponding to the locations of leads used to acquire the measured ECG signals (e.g., 12 lead ECG) of the patient. A simulated ECG signal is calculated using the body surface potentials calculated at the ECG lead positions, and ECG features, such as the duration of the QRS complex $\Delta_{QRS}$ and the electrical axis angle $\alpha_{EA}$ can be derived automatically from the simulated ECG signal. It should be noted that in the above description a homogeneous torso model is employed. However, this can be extended to a heterogeneous torso model that incorporates muscle, lungs, bones, fat and other tissues, as identified in medical images. Each tissue would then have different electrical conductivity.

Figure 3:
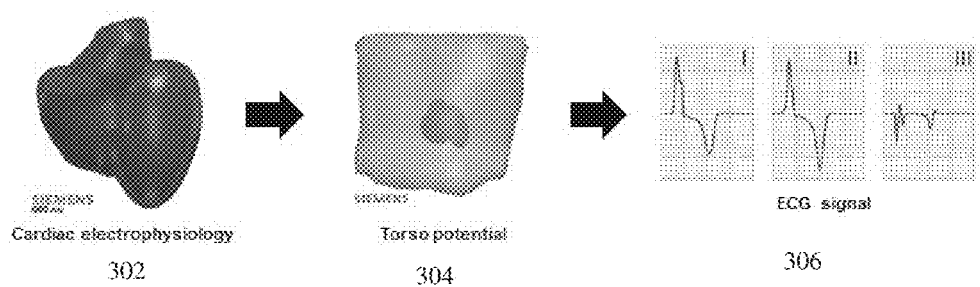
FIG. 3 illustrates exemplary results for simulating cardiac electrophysiology using a computational cardiac electrophysiology model.

FIG. 3 illustrates exemplary results for simulating cardiac electrophysiology using a computational cardiac EP model. As shown in FIG. 3, image 302 shows a map of cardiac transmembrane potentials resulting from simulating cardiac EP using the computational cardiac EP model, image 304 shows a map of torso potentials generated from the simulated cardiac transmembrane potentials, and image 306 shows an ECG signal generated based on torso potentials at ECG lead locations.

The computational cardiac EP model needs to be personalized in order to be predictive for a specific patient. The computational cardiac EP model can be initialized for standard value for electrical diffusivity c and action potential duration APDd, and these values are then adjusted in a number of simulations of the cardiac EP model based on the EP measurements of the patient. The computational cardiac EP model can be initialized with high diffusivity coefficients on the endocardia to mimic the effect of Purkinje fibers, and lower diffusivity throughout the myocardium. The knowledge of tissue integrity from the patient-specific anatomical model can be used to constrain the patient-specific parameter estimation process. In particular, border zone tissues are assigned slower electrical conductivities (diffusivities) c but larger action potential durations APDd, while scars or necrosis regions resulting from ablation have even slower conductivities (up to zero conductivity). Accordingly, predetermined values for c and APDd are assigned to border zone and scar nodes of the patient-specific anatomical model and these values are used to constrain the parameter estimation. The personalization techniques described herein are independent of the type of intervention being performed as can be similarly applied to all types of interventions (e.g., VT, Afib, etc.).

In one embodiment the registered invasive EP mapping measurements are used to personalize the electrical conductivity c and the action potential duration APDd parameters of the cardiac EP model. It is to be understood that the present invention is not limited to these particular parameters and other parameters of the EP model can be estimated as well. In a first stage, the personalization procedure can be formulated as an optimization problem. After registration of the invasive EP mapping data to the patient-specific anatomical heart model as previously described, an optimizer is employed to minimize the point-wise difference between calculated activation times using the cardiac EP model and measured activation times based on the invasive EP mapping measurements to estimate the electrical conductivity parameters over the nodes of the patient-specific anatomical heart model. For increased estimation convergence and robustness to local minima, a coarse-to-fine strategy can be employed. In the coarse-to-fine strategy, a value for c is first estimated for both ventricles. Areas with larger errors are then partitioned, and one c value per partition is estimated, initialized to the value of the previous step. The procedure is then iterated until convergence. Local APDd can be estimated based on the EP mapping measurements of the patient in a similar fashion. The two steps are alternated until global convergence. Knowledge of tissue integrity is directly used in the estimation process as constraints: border zone tissues have slower conductivities c but larger APDd, while scars have even slower conductivities (up to zero conductivity). This personalization method works for both contact mapping and basket catheter systems.

According to an advantageous embodiment of the present invention, the personalized parameters of the patient-specific cardiac EP model can be updated online during the intervention from newly acquired EP maps, as more data is acquired. When new EP measurements are acquired and mapped to the anatomical model, they are given as input to the estimation procedure. Similarly, segmented lesions (necrosis regions resulting from ablation) are used to update the model of tissue substrate. The optimizer is then run again starting from the current estimates of c and APDd. Areas with large errors are identified and partitioned through thresholding and the optimizer is run again as described above.

In another embodiment, machine learning methods can be utilized to estimate parameters of the cardiac EP model based on the EP measurements of the patient. In an offline training stage, a large database of activation maps and APDd maps (or any other EP measurements) are created using the computational cardiac EP model with different parameter values. Advanced non-linear manifold learning techniques are utilized to train a regression function, and the personalized parameters are estimated on-line by applying the trained regression function to regress the local values of c and APDd given the local activation maps of the measured EP data of the patient.

In another embodiment, body surface potential measurements, such as ECG measurements of body surface mapping measurements, can be used to estimate the personalized parameters of the cardiac EP model, for example using the method described in U.S. Patent Publication No. 2015/0042646, entitled "System and Method for Patient Specific Planning and Guidance of Electrophysiology Interventions," which is incorporated herein by reference in its entirety. The ECG measurements can be used instead of the invasive EP maps or in order to enhance the personalization performed using the invasive EP maps. As described above, the cardiac EP model is linked to a boundary element model of torso potential conductivity. In a possible implementation, a machine learning method can then be performed to automatically infer electrical conductivity c and APDd from measured torso potentials. In an offline training stage, a database of torso potentials, cardiac potentials, and model parameters is created using the forward model (cardiac EP model). Non-linear manifold learning approaches can be utilized to train a regression function to regress c and APDd from torso potentials. In the on-line personalized parameter estimation, the regression function is applied to estimate c and APDd from the measured torso potentials of the patient. This approach is not only extremely computationally efficient, but can also provide information on the uncertainty associated with the estimated cardiac parameters. The system is therefore able to quantify the inverse mapping uncertainty with respect to the number and position of the body surface leads. This gives the optimal spatial configuration of the torso leads necessary to achieve the required accuracy for cardiac EP modeling (measurement localization optimization). A coarse-to-fine approach can be used to deal with model complexity and ill-posedness.

In another possible implementation for estimating the personalized parameters of the cardiac EP model based on the body surface potential measurements, back-propagation and inverse modeling can be performed. In this case, the body surface potential measurements (torso potentials) are back-propagated to estimate cardiac potentials, which are compared to simulated cardiac potentials computed using the cardiac EP model. The c and APDd parameters of the cardiac EP model are updated using optimization techniques to reduce an error (measured by a cost function) between the simulated cardiac potentials and cardiac potentials calculated from the body surface potential measurements. These steps can be repeated until convergence. It is also possible, that simulated torso potentials and/or a simulated ECG signal are computed from the transmembrane potentials simulated using the cardiac EP model, as described above, and optimization techniques are utilized to adjust the c and APDd parameters of the cardiac EP model to minimize a cost function between the simulated torso potentials (or the simulated ECG signal) and the measured torso potentials (or the measured ECG signal). These steps can be repeated until convergence.

According to an advantageous embodiment of the present invention, in addition to personalizing the parameters of the cardiac EP model, the EP measurements of the patient can be used to guide the characterization or segmentation of the cardiac tissue. The patient-specific computational cardiac EP model defines a relationship between the properties of the cardiac tissue and the measured EP data (e.g., invasive EP measurements, ECG, body surface potentials). Therefore, the identification of anatomical structures from images can be constrained by the functional information provided by the model. In an advantageous embodiment, the size and location of the scar tissue and the border zone is estimated based on the medical image data and included in the patient-specific anatomical heart model as described above. The segmentation of the border zone and/or scar tissue is then optimized by adjusting the size and location of the border zone and/or scar tissue in the patient-specific anatomical model based on one or more of the personalization techniques described above. This results in a model-based segmentation of the cardiac tissue including functional information, that is a model-based histology. In a possible implementation, parameters representing the size and the location of the border zone and/or scar tissue can be optimized along with the electrical conductivity (diffusivity) c and action potential duration APDd parameters of the computational cardiac EP model in an iterative algorithm. As described above, c and APDd are constrained by the scar tissue and border zone segmentation. In each iteration of the estimation algorithm, cardiac EP is simulated by the cardiac EP model using the current parameters for c, APDd, and the size and location of the border zone and/or scar tissue; optimization techniques are used to adjust the values for c, APDd, and the size and location parameters of the border zone and/or scar tissue to reduce an error between the simulated cardiac EP and the measured EP data of the patient. These steps can be iterated until convergence. Alternatively, machine learning methods can be used, as described above, to train a regression function that estimates c, APDd, and the size and location parameters of the border zone and/or scar tissue based on the EP measurements of the patient.

Returning to FIG. 1, at step 110, virtual EP interventions are performed using the patient-specific computational cardiac EP model. In each virtual EP intervention, one or more cardiac EP simulations are performed using the patient-specific computational cardiac EP model resulting from personalizing the tissue parameters (e.g., c and APDd) of the computational cardiac EP model in step 108. For each of the patient-specific cardiac EP simulations, simulation results can be output. For example, cardiac EP maps (e.g., transmembrane potential maps, activation time maps, depolarization time maps, repolarization time maps, etc.) can be visualized and displayed on a display device. In addition, torso potentials and a simulated ECG signal can be computed from the simulated transmembrane potentials for each patient-specific cardiac EP simulation. The simulated ECG signal can be displayed on a display device and a map of the torso potentials can be visualized and displayed on the display device. 3D maps of the electrical diffusivity c and/or the action potential duration APDd of the cardiac tissue can be visualized based on the personalized parameters of the patient-specific cardiac EP model.

The virtual EP interventions can be used to test different EP therapies and answer various questions, such as, but not limited to: 1) is VT inducible in the patient or not, and which protocol will induce it? 2) What is the optimal VT ablation target (e.g., minimum amount of ablation while minimizing risks of arrhythmias)? 3) Will the therapy successfully treat the patient for arrhythmias (by trying with the model different excitations/heart rates)? All these questions can be probed on the model using interactive or automatic virtual EP interventions.

Once the patient-specific cardiac EP model is estimated, one or more pacing locations are selected along with the pacing protocol, and N seconds (e.g. 30 s) of cardiac EP is simulated using the patient-specific EP model. As described above virtual pacing is performed by adding a stimulus current $J_{stim}(x)$ to the patient-specific cardiac EP model at the pacing locations according to the pacing protocol. The resulting ECG is calculated, from which cycle length and ECG morphology are derived to be used for decision making. The virtual pacing can be repeated at various locations and using various pacing protocols to find a best pacing location and best pacing protocol. For example, the virtual pacing can be performed to find a pacing location and pacing protocol that will induce VT. In one implementation, the pacing locations and pacing protocols are interactively input by a user. For example, the user can input the pacing locations on a visualization of the patient-specific anatomical heart model or a visualization of an EP map on the patient-specific anatomical heart model or on an interventional image using a mouse, touch screen, etc. The virtual pacing can then be performed in real-time or near real-time in response to the user input. In another implementation, various pacing locations and pacing protocols can be tested automatically in an automatic scan. In this case, the user would receive (e.g., by displaying on a display device) pacing locations and protocols candidates along with the resulting cardiac EP and ECG. It is also possible that a best pacing location and pacing protocol is selected automatically based on the automatically performed virtual pacing and provided to the user. For example, different locations can be automatically graded based on the results of the virtual pacings and a color-map showing the graded pacing locations can be generated and displayed.

Virtual ablations can be performed in a similar fashion to the virtual pacing. For example, the user can interactively select ablation locations and ablation protocols to virtually ablate areas of the anatomy. Alternatively, virtual ablations can be automatically performed for various ablation locations and ablation protocols. In a possible implementation, the ablated area resulting from a virtual ablation is automatically given scar parameters (small/no conductivity). In another possible implementation, a model of ablation therapy is utilized to simulate the effects of heat transfer and cellular necrosis. The model of ablation therapy can be implemented as described in International Publication No. WO 2014/133924 A1, entitled "System and Method for Interactive Patient-Specific Simulation of Radiofrequency Ablation Therapy," or U.S. patent application Ser. No. 14/622,022, filed Feb. 13, 2015, entitled "System and Method for Personalized Computation of Tissue Ablation Extent Based on Medical Images," which are incorporated herein by reference in their entirety. In both cases, the computation is performed interactively, and the EP simulation using the patient-specific cardiac EP model is recalculated on the new tissue model, yielding predictors of therapy outcome. Different heart rates (e.g., corresponding to different excitation states of the patient) can also be tested. The different heart rates can be input by the user or selected automatically. The patient-specific cardiac EP model receives each desired heart rate, and several cycles of cardiac EP are simulated at the desired heart rate. Since the cellular model properties adapt to the heart rate (restitution curve), arrhythmias promoted by increased effort can be detected before performing an ablation procedure by varying the heart rate in the virtual ablation, and therefore treated in advance during the same ablation procedure.

Figure 4:
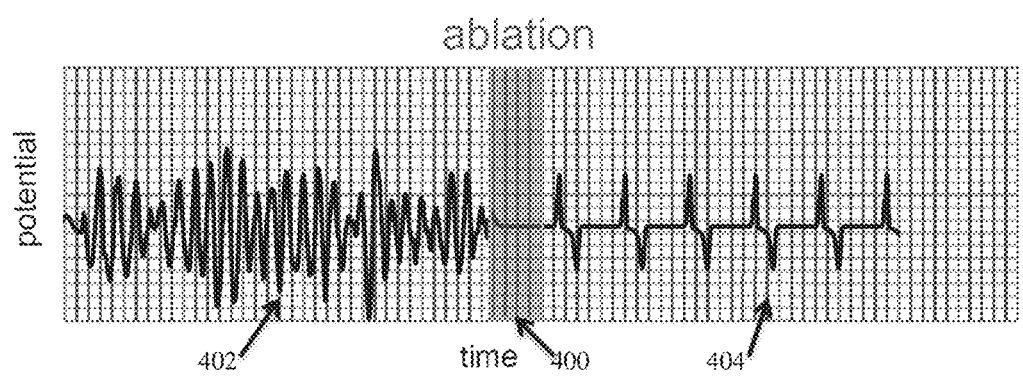
FIG. 4 illustrates an exemplary electrocardiogram (ECG) signal resulting from a successful virtual ablation.

A target ablation location and target ablation protocol can be determined based on the virtual ablations by finding an ablation location and protocol that causes a minimal ablation region but still successfully treats the patient's VT. For example, the ECG signals resulting from EP simulation after each virtual ablation can be displayed and user can determine which ablation therapies are successful from the ECG signals. Alternatively, a best ablation location (or locations) can be automatically determined based on the virtual ablations and the best ablation location can be provided to the user, for example, by displaying a map highlighting a best ablation location or a color map showing gradings of various possible ablation locations. FIG. 4 illustrates an exemplary electrocardiogram (ECG) signal resulting from a successful virtual ablation. In particular, FIG. 4 shows the ECG signal 402 before the ablation 400, which is indicative of an arrhythmia, as well as the ECG signal 404 after the ablation 400.

The virtual EP interventions can be enhanced by leveraging the interventional setup. In particular, once the pacing/ablation location is defined, the catheters can be detected in the actual intervention from the interventional images and tracked. A trajectory of the catheter can be displayed to show the path to reach the ablation target. In a possible embodiment, a virtual reality system can be implemented where the user does not "point-and-click" on the organ on a conventional display to select locations for virtual pacing and virtual ablation, but rather navigates a virtual catheter inside the virtual reality representation of heart, implemented using virtual reality technology and mimicking realistic conditions. The degrees of freedom associated with catheter handling are implemented through knobs or specialized input devices, such as haptic sensors, joysticks, etc.

In addition to ablation therapies, other EP therapies, such as CRT therapies can be guided using the virtual EP interventions. In the case of CRT, the virtual EP interventions can be implemented to test different lead positions and pacing protocols to determine target lead positions and pacing protocols for the CRT therapy.

Returning to FIG. 1, at step 112, pacing targets and ablation targets based on the virtual electrophysiology interventions are output. Other simulation results (e.g., pacing protocol, ablation protocol, ECG signals, EP maps, etc.) of the virtual electrophysiology simulations can be output as well. In a possible implementation, the pacing targets and ablation targets can be output by displaying the pacing targets and ablation targets on a visualization of the patient-specific anatomical heart model. For example, the pacing target locations and ablation target locations can be highlighted on the visualization of the patient-specific anatomical heart model or a color map indicating grades for various pacing target locations or ablation target locations can be overlaid on the visualization of the patient-specific anatomical heart model. In another possible implementation the pacing targets and ablation targets can be output by displaying the pacing targets and ablation targets on an interventional image, such as an interventional MRI image, acquired during the EP intervention. For example, locations of pacing targets or ablation targets can be highlighted on the interventional image or a color map indicating grades for various pacing target locations or ablation target locations can be overlaid on the interventional image. The interventional image can then be used to guide the EP intervention.

At step 114, ablation is performed at an ablation target in the patient's heart. The electrophysiologist performing the ablation can use the pacing targets and ablation targets output based on the virtual EP interventions to guide the pacing and ablation. For example, for ablation therapy for treating VT, the electrophysiologist can pace the patient's heart using an electrode at a target pacing location to induce VT and then perform ablation using an ablation catheter at a target ablation location to destroy the tissue in order to suppress the VT. The pacing protocol and the ablation protocol used in the ablation procedure can be determined using the virtual EP interventions.

At step 116, an ablated region resulting from the ablation is quantified. The ablated region, which can also be referred to as a "lesion", refers to a region of cellular necrosis resulting from an ablation. Tissue in this ablated region is dead and is no longer conductive. Since the ablation modifies the tissue integrity during the intervention, it is important to quantify the extent of the ablated region not only for therapy monitoring, but also to update the patient-specific anatomical heart model and patient-specific cardiac EP model with new tissue properties in order to ensure that future predictions using the patient-specific anatomical heart model and the patient-specific cardiac EP model are accurate. In one embodiment, the ablated region can be automatically segmented from an interventional image (e.g., interventional MRI) acquired during the intervention after the ablation session. This image segmentation problem can be addressed in two stages. First, an image-based algorithm is used to extract the lesion from the image. At each ablation in the ablation session, the ablation catheter position is recorded and mapped to the anatomical model. At the end of the ablation session, an interventional image of the ablated region is acquired, and rigidly registered to the patient-specific anatomical heart model. Regions of interests (ROI) are extracted around the ablation catheter positions in the registered interventional image and a histogram-based clustering method is employed to segment the ablated tissue from the neighboring tissue in each ROI. Next, because the local grey-level distribution is unknown and probably not Gaussian, the mean-shift algorithm is used to automatically find the most hypo-intense mode related to the ablated region for each ROI. This procedure is performed independently for each ROI.

The image-based segmentation of the ablated region may be hindered by the presence of edema. In another embodiment, the image segmentation approach can be enhanced by directly modeling the ablative process itself. A computational model of heat transfer and cellular necrosis can be used to simulate the ablation and computed a simulated necrosis region. The ablation parameters used for the actual ablation are input into the model of heat transfer and cellular necrosis and the extent of the necrosis is computed. After a first ablation during an intervention for a patient, the ablated region is segmented in an interventional image and the model of heat transfer and cellular necrosis is personalized for that patient by estimating tissue parameters of the model that minimize a difference between the segmented ablated region in the interventional image and the simulated ablated region computed using the model of heat transfer and cellular necrosis. Once personalized, ablation extents of other ablations at other targets during the intervention can be directly computed with the personalized model of heat transfer and cellular necrosis. Additional details regarding the model of heat transfer and cellular necrosis and personalizing the model are described in International Publication No. WO 2014/133924 A1, entitled "System and Method for Interactive Patient-Specific Simulation of Radiofrequency Ablation Therapy," and U.S. patent application Ser. No. 14/622,022, filed Feb. 13, 2015, entitled "System and Method for Personalized Computation of Tissue Ablation Extent Based on Medical Images," which are incorporated herein by reference in their entirety.

At step 118, the patient-specific anatomical heart model and the patient-specific computational cardiac EP model are updated based on the ablated region. Once the ablated region resulting from an ablation session are quantified, either by segmenting the ablated region in an interventional image or by computing the ablated region using the personalized model of heat transfer and cellular necrosis, the patient-specific anatomical heart model is updated by labeling nodes of the patient-specific anatomical heart model in the ablated region. The patient-specific computational cardiac EP model is then updated by adjusting the parameter values (e.g., electrical conductivity c and action potential duration APDd) of the patient-specific computational cardiac EP model for the nodes of the patient-specific anatomical heart model in the ablated region. In a possible implementation, the tissue in the ablated region can be assigned predetermined parameters, such as scar parameters (little or no conductivity). In another possible implementation, tissue parameters of the patient-specific cardiac EP model for the tissue in the ablated region can be updated based on corresponding tissue parameters for that tissue computed by the personalized model of heat transfer and cellular necrosis.

Once the patient-specific anatomical heart model and the patient-specific computational EP model are updated, the method of FIG. 1 returns to step 110 and additional virtual EP interventions are performed using the updated patient-specific computational cardiac EP model. For example, additional virtual EP interventions can be performed to guide additional ablation sessions in the electrophysiological intervention. Steps 110-118 of FIG. 1 can be repeated to provide real-time on-line guidance of the electrophysiological intervention until completion of the electrophysiological intervention.

Although the method of FIG. 1 is described above as using an interventional MRI system, the present invention is not limited thereto and other interventional setups can be used as well. For example, the method of FIG. 1 can be similarly applied to a hybrid X-ray/MRI (XMR) setup, where both X-ray and MRI image are acquired. In this implementation, the MRI data is overlaid on fluoroscopy images acquired during catheter navigation. Catheter tracking in the fluoroscopy images can be performed to identify the position of the catheter in the 3D patient-specific anatomical heart model and/or to display trajectories towards pacing and ablation targets. Ablation and pacing targets used to guide the intervention can also be displayed in the 2D fluoroscopy images acquired during catheter navigation.

As described above, the method of FIG. 1 estimates a patient-specific cardiac EP model and uses the patient-specific cardiac EP model to perform the virtual EP interventions. In a possible embodiment, the cardiac EP model may be a cardiac electromechanics model that couples a model of cardiac biomechanics to the computational model of cardiac EP to simulate cardiac EP and cardiac biomechanics (movement of the heart) over a period of time. The model of cardiac biomechanics is coupled to the model of cardiac EP described above and simulates deformation of the patient-specific anatomical model by solving the dynamics equation $M\ddot{u}+C\dot{u}+Ku=F_a+F_p+F_b$, where $\ddot{u}$, $\dot{u}$ and $u$ represent accelerations, velocities and displacements, respectively, of the mesh nodes, and M, K and C are the mass matrix, internal elastic stiffness matrix and Rayleigh damping matrix, respectively. $F_a$, $F_p$ and $F_b$ model active stress, ventricular pressure, and mechanical boundary conditions, respectively. The active stress forces $F_a$ can be computed by a model that expresses the active Cauchy stress tensor in terms of an action potential. Accordingly, the action potential computed by the model of cardiac electrophysiology at each time step for each node in the patient-specific anatomical heart model is used to determine the active stress force $F_a$ applied at that node in the model of cardiac biomechanics. The model for computing the active stress is mainly governed by three parameters, namely the maximum contraction that can be reached by a cell and the ATP binding and release rates. The model simplifies the true myocyte contraction and thus only approximates the behavior of the complex underlying bio-physical phenomena. This allows for the number of parameters to be rather low while clinically observable, enabling robust personalization of the model. More advanced models could similarly be employed without significant modification. The passive stress $F_p$ can be computed using linear models or orthotropic models, such as the orthotropic Holzapfel-Ogden (H-O) model. The H-O model is derived from considerations of the myocardial tissue structure, meaning that cardiac tissue shows different behavior whether it is stretched along the fiber direction, perpendicular to the fiber, etc. The H-O model comprises eight material constants, which are contained within an exponential stress-strain energy function. Reformulating the energy using multiplicative Jacobian energy decomposition (MJED) or Total Lagrangian Explicit Dynamics (TLED) formulation allows for efficient computation of patient-specific tissue biomechanics. Both the effect of arteries and atria on ventricular motion and a pericardium constraint are considered within the biomechanical model as mechanical boundary conditions, which account for the force vectors $F_b$. In the case in which the cardiac EP model is a cardiac electromechanics model, the method described above for personalizing the cardiac EP model can be modified to add a step of estimating patient-specific biomechanical tissue parameters (e.g., stiffness and maximum active stress) based a comparison between observed heart movement in the dynamic cardiac medical images of the patient and simulated heart movement using the model of cardiac biomechanics at each iteration. In this case the cardiac electromechanics model simulates cardiac electromechanics (electrophysiology and biomechanics); the cardiac electrophysiology parameters (e.g., electrical diffusivity c and action potential duration APDd) and the cardiac biomechanics parameters (e.g., tissue stiffness and maximum active stress) are estimated based on the simulated cardiac electromechanics, the EP measurements of the patient, and the observed heart movement of the patient.

Figure 5:
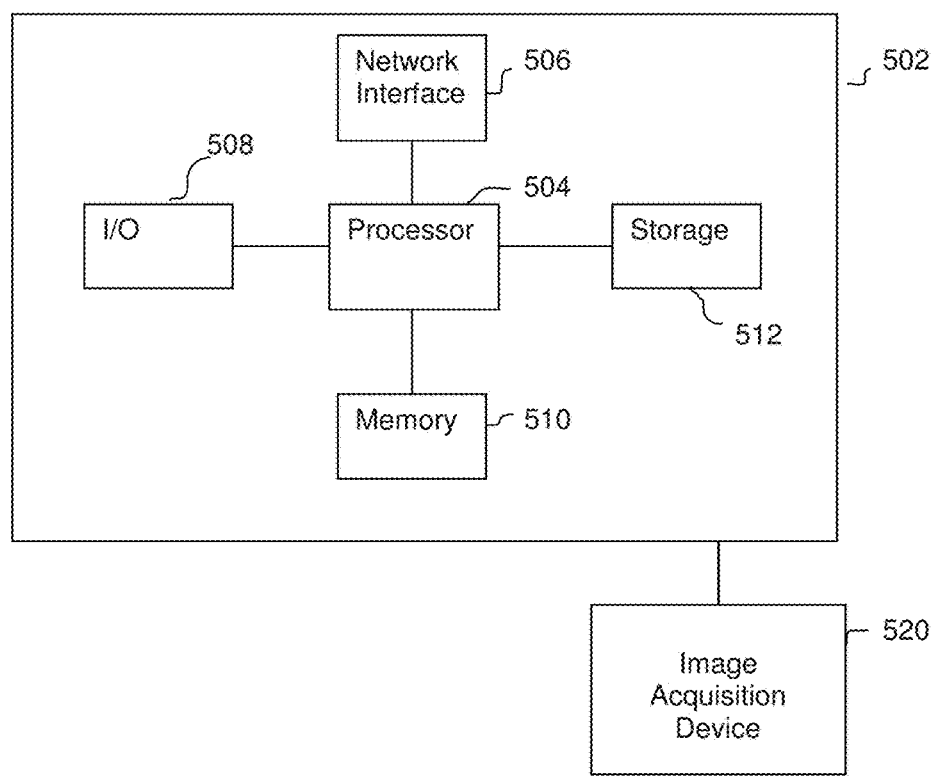
FIG. 5 is a high-level block diagram of a computer capable of implementing the present invention.

The above-described methods for patient-specific planning and guidance of electrophysiological interventions can be implemented on a computer using well-known computer processors, memory units, storage devices, computer software, and other components. A high-level block diagram of such a computer is illustrated in FIG. 5. Computer 502 contains a processor 504, which controls the overall operation of the computer 502 by executing computer program instructions which define such operation. The computer program instructions may be stored in a storage device 512 (e.g., magnetic disk) and loaded into memory 510 when execution of the computer program instructions is desired. Thus, the steps of the method of FIG. 1 may be defined by the computer program instructions stored in the memory 510 and/or storage 512 and controlled by the processor 504 executing the computer program instructions. The processor 502 may include one or more central processing unit (CPU) and/or one or more graphics processing unit (GPU) or general purpose graphics processing unit (GPGPU). An image acquisition device 520, such as an MRI scanning device, CT scanning device, C-arm image acquisition device, Ultrasound device, etc., can be connected to the computer 502 to input image data to the computer 502. It is possible to implement the image acquisition device 520 and the computer 502 as one device. It is also possible that the image acquisition device 520 and the computer 502 communicate wirelessly through a network. The computer 502 also includes one or more network interfaces 506 for communicating with other devices via a network. The computer 502 also includes other input/output devices 508 that enable user interaction with the computer 502 (e.g., display, keyboard, mouse, speakers, buttons, etc.). Such input/output devices 508 may be used in conjunction with a set of computer programs as an annotation tool to annotate volumes received from the image acquisition device 520. One skilled in the art will recognize that an implementation of an actual computer could contain other components as well, and that FIG. 5 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for patient-specific guidance of an electrophysiological intervention, comprising:
   generating a patient-specific anatomical heart model from medical image data of a patient;
   generating a patient-specific cardiac electrophysiology model based on the patient-specific anatomical heart model and electrophysiology measurements of the patient;
   performing one or more virtual electrophysiological interventions using the patient-specific cardiac electrophysiology model;

displaying one or more pacing targets or ablation targets based on the one or more virtual electrophysiological interventions; and updating the patient-specific cardiac electrophysiology model based on results of the electrophysiological intervention.

2. The method of claim 1, wherein updating the patient-specific cardiac electrophysiology model based on results of the electrophysiological intervention comprises:

updating the patient-specific cardiac electrophysiology model based on results of an ablation performed in the electrophysiological intervention.

3. The method of claim 2, wherein updating the patient-specific cardiac electrophysiology model based on results of an ablation performed in the electrophysiological intervention comprises:

quantifying an ablated region of the patient's heart resulting from the ablation performed in the electrophysiological intervention;

updating the patient-specific anatomical heart model to include the ablated region in the patient-specific anatomical heart model; and updating the patient-specific cardiac electrophysiology model based on the updated patient-specific anatomical heart model.

4. The method of claim 3, wherein quantifying an ablated region of the patient's heart resulting from the ablation performed in the electrophysiological intervention comprises:

segmenting a necrosis region in an interventional image acquired during the electrophysiological intervention.

5. The method of claim 4, further comprising:

personalizing a computational model of heat transfer and cellular necrosis for the patient based on a difference between the segmented necrosis region in the interventional image and a simulated necrosis region computed using the model of heat transfer and cellular necrosis.

6. The method of claim 3, wherein quantifying an ablated region of the patient's heart resulting from the ablation performed in the electrophysiological intervention comprises:

computing a necrosis region based on parameters of the ablation performed in the electrophysiological intervention using a patient-specific model of heat transfer and cellular necrosis personalized for the patient based on results of a previous ablation performed in the electrophysiological intervention.

7. The method of claim 2, wherein the step of updating the patient-specific cardiac electrophysiology model based on results of an ablation performed in the electrophysiological intervention is performed in real-time during the electrophysiological intervention in response to the ablation performed in the electrophysiological intervention.

8. The method of claim 1, wherein generating a patient-specific anatomical heart model from medical image data of a patient comprises:

extracting a multi-component patient-specific heart morphology model from the medical image data and fusing the multi-component patient-specific heart morphology model into a single heart model;

segmenting at least one of scar or border zone tissue in the medical image data mapping the segmented at least one of scar or border zone tissue to the single heart model; and generating a model of myocardium fiber architecture based on the single heart model.

9. The method of claim 1, wherein generating a patient-specific cardiac electrophysiology model based on the patient-specific anatomical heart model and electrophysiology measurements of the patient comprises:

registering the electrophysiology measurements of the patient to the patient-specific anatomical heart model; and estimating patient-specific parameters for the patient-specific cardiac electrophysiology model based on the registered electrophysiology measurements of the patient.

10. The method of claim 9, wherein the electrophysiology measurements of the patient are invasive cardiac electrophysiology measurements acquired using a catheter probe and registering the electrophysiology measurements of the patient to the patient-specific anatomical heart model comprises:

detecting a respective location of the catheter probe in each of a plurality of interventional images;

calculating a transformation of electrophysiology measurements acquired by the catheter probe at each respective location to the patient-specific anatomical heart model based on the respective location of the catheter probe in each of the plurality of interventional images; and mapping a plurality of subsequent measurements by the catheter probe to the patient-specific anatomical heart model using the transformation.

11. The method of claim 9, wherein the electrophysiology measurements of the patient are invasive cardiac electrophysiology measurements acquired using a catheter basket and registering the electrophysiology measurements of the patient to the patient-specific anatomical heart model comprises:

calculating a transformation to register an interventional image acquired when the catheter basket is anchored in a heart of the patient to the patient-specific anatomical heart model;

registering the catheter basket to the patient-specific anatomical heart model using the transformation; and mapping the cardiac electrophysiology measurements acquired by the catheter to the patient-specific anatomical heart model.

12. The method of claim 9, wherein the electrophysiology measurements of the patient are body surface potential measurements of the patient and registering the electrophysiology measurements of the patient to the patient-specific anatomical heart model comprises:

segmenting a torso model for the patient from the medical image data;

registering the torso model to the patient-specific anatomical heart model;

mapping the body surface potential measurements of the patient to the torso model; and back-projecting body surface potentials to the patient-specific anatomical heart.

13. The method of claim 1, wherein the electrophysiology measurements of the patient include at least one of invasive cardiac electrophysiology mappings, ECG measurements, or body surface mappings (BSM).

14. The method of claim 1, wherein generating a patient-specific cardiac electrophysiology model based on the patient-specific anatomical heart model and electrophysiology measurements of the patient comprises:

estimating patient-specific electrical diffusivity and action potential duration parameters of the patient-specific cardiac electrophysiology model based on the patient-specific anatomical heart model and the electrophysiology measurements of the patient.

15. The method of claim 1, wherein generating a patient-specific cardiac electrophysiology model based on the patient-specific anatomical heart model and electrophysiology measurements of the patient comprises:
    simulating cardiac electrophysiology in the patient-specific anatomical heart model using a computational cardiac electrophysiology model; and
    estimating patient-specific parameters of the cardiac electrophysiology model to minimize an error between the simulated cardiac electrophysiology and the electrophysiology measurements of the patient.

16. The method of claim 15, wherein simulating cardiac electrophysiology in the patient-specific anatomical heart model using a computational cardiac electrophysiology model comprises:
    generating a Cartesian grid domain using the patient-specific anatomical heart model; and
    calculating transmembrane potential variation over time at each of a plurality of nodes of the patient-specific anatomical heart model in the Cartesian grid domain by computing a solution of the computational cardiac electrophysiology model for each of the plurality of nodes using a Lattice-Boltzmann method for electrophysiology.

17. The method of claim 15, wherein the electrophysiology measurements of the patient are invasive cardiac electrophysiology measurements and estimating patient-specific parameters of the cardiac electrophysiology model to minimize an error between the simulated cardiac electrophysiology and the electrophysiology measurements of the patient comprises:
    estimating patient-specific parameters of the cardiac electrophysiology model that minimize an error between activation times of the simulated cardiac electrophysiology and activation times of the invasive cardiac electrophysiology measurements.

18. The method of claim 15, wherein the electrophysiology measurements of the patient include body surface potential measurements and estimating patient-specific parameters of the cardiac electrophysiology model to reduce an error between the simulated cardiac electrophysiology and the electrophysiology measurements of the patient comprises:
    estimating patient-specific parameters of the cardiac electrophysiology model that reduce an error between the simulated cardiac electrophysiology and back-projected cardiac potentials calculated from the body surface measurements.

19. The method of claim 15, wherein the electrophysiology measurements of the patient include body surface potential measurements and estimating patient-specific parameters of the cardiac electrophysiology model to reduce an error between the simulated cardiac electrophysiology and the electrophysiology measurements of the patient comprises:
    estimating patient-specific parameters of the cardiac electrophysiology model that reduce an error between simulated body surface potentials calculated from the simulated cardiac electrophysiology and the body surface potential measurements.

20. The method of claim 15, wherein the estimating of the patient-specific parameters of the cardiac electrophysiology model to minimize the error between the simulated cardiac electrophysiology and the electrophysiology measurements of the patient is constrained by scar and border zone tissue in the patient-specific anatomical heart model.

21. The method of claim 15, wherein estimating patient-specific parameters of the cardiac electrophysiology model to minimize an error between the simulated cardiac electrophysiology and the electrophysiology measurements of the patient comprises:
    estimating the patient-specific parameters of the patient-specific cardiac electrophysiology model and adjusting a location and size of at least one of scar or border zone tissue in the patient-specific anatomical heart model to minimize the error between the simulated cardiac electrophysiology and the electrophysiology measurements of the patient.

22. The method of claim 1, wherein updating the patient-specific cardiac electrophysiology model based on results of the electrophysiological intervention comprises:
    updating the patient-specific cardiac electrophysiology model based on newly acquired electrophysiology measurements of the patient during the electrophysiological intervention.

23. The method of claim 1, wherein generating a patient-specific cardiac electrophysiology model based on the patient-specific anatomical heart model and electrophysiology measurements of the patient comprises:
    estimating patient-specific parameters of the patient-specific cardiac electrophysiology model based on the electrophysiology measurements of the patient using a trained regression function.

24. The method of claim 1, wherein performing one or more virtual electrophysiological interventions using the patient-specific cardiac electrophysiology model comprises:
    receiving user inputs selecting one or more pacing locations and one or more pacing protocols;
    performing a respective cardiac electrophysiology intervention simulation using the patient-specific cardiac electrophysiology model with a stimulus current added at the pacing location according to the pacing protocol for each of the pacing locations and pacing protocols; and
    displaying a visualization of the simulated cardiac electrophysiology resulting from each respective cardiac electrophysiology intervention simulation.

25. The method of claim 24, wherein displaying a visualization of the simulated cardiac electrophysiology resulting from each respective cardiac electrophysiology intervention simulation comprises:
    displaying at least one of an ECG signal or an electrophysiology map calculated from each respective cardiac electrophysiology intervention simulation.

26. The method of claim 1, wherein performing one or more virtual electrophysiological interventions using the patient-specific cardiac electrophysiology model comprises:
    automatically selecting a plurality of pacing locations and pacing protocols at which to perform virtual pacing; and
    performing a respective cardiac electrophysiology intervention simulation using the patient-specific cardiac electrophysiology model with a stimulus current added at the pacing location according to the pacing protocol for each of the plurality of pacing locations and pacing protocols.

27. The method of claim 26, wherein performing one or more virtual electrophysiological interventions using the patient-specific cardiac electrophysiology model further comprises:

automatically determining a target pacing location and pacing protocol based on the respective cardiac electrophysiology intervention simulations for the plurality of pacing locations and pacing protocols.

28. The method of claim 1, wherein performing one or more virtual electrophysiological interventions using the patient-specific cardiac electrophysiology model comprises:
receiving user inputs selecting one or more ablation locations and one or more ablation protocols;
performing a respective cardiac electrophysiology intervention simulation using the patient-specific cardiac electrophysiology model for each of the ablation locations and ablation protocols; and
displaying a visualization of the simulated cardiac electrophysiology resulting from each respective cardiac electrophysiology intervention simulation.

29. The method of claim 28, wherein displaying a visualization of the simulated cardiac electrophysiology resulting from each respective cardiac electrophysiology intervention simulation comprises:
displaying at least one of an ECG signal or an electrophysiology map calculated from each respective cardiac electrophysiology intervention simulation.

30. The method of claim 1, wherein performing one or more virtual electrophysiological interventions using the patient-specific cardiac electrophysiology model comprises:
a plurality of ablation locations and ablation protocols at which to perform virtual ablation; and
performing a respective cardiac electrophysiology intervention simulation using the patient-specific cardiac electrophysiology model for each of the plurality of ablation locations and ablation protocols.

31. The method of claim 30, wherein performing one or more virtual electrophysiological interventions using the patient-specific cardiac electrophysiology model further comprises:
automatically determining a target ablation location and ablation protocol based on the respective cardiac electrophysiology intervention simulations for the plurality of ablation locations and ablation protocols.

32. The method of claim 1, wherein performing one or more virtual electrophysiological interventions using the patient-specific cardiac electrophysiology model comprises:
performing virtual pacing at a plurality of pacing locations and pacing protocols to determine a target pacing location and pacing protocol that induces a cardiac arrhythmia; and
performing virtual ablation at a plurality of ablation locations and ablation protocols to determine a target ablation location and ablation protocol that treats the cardiac arrhythmia.

33. The method of claim 1, wherein performing one or more virtual electrophysiological interventions using the patient-specific cardiac electrophysiology model comprises:
performing virtual pacing at a plurality of pacing locations and pacing protocols to determine target pacing locations and pacing protocols for a cardiac resynchronization therapy.

34. The method of claim 1, wherein displaying one or more pacing targets or ablation targets based on the one or more virtual electrophysiological interventions comprises:
displaying the one or more pacing targets or ablation targets on a visualization of the patient-specific anatomical heart model.

35. The method of claim 1, wherein displaying one or more pacing targets or ablation targets based on the one or more virtual electrophysiological interventions comprises:
displaying the one or more pacing targets or ablation targets on an interventional image acquired during the electrophysiological intervention.

36. The method of claim 1, wherein the patient-specific cardiac electrophysiology model is a patient-specific cardiac electromechanics model.

37. An apparatus for patient-specific guidance of an electrophysiological intervention, comprising:
means for generating a patient-specific anatomical heart model from medical image data of a patient;
means for generating a patient-specific cardiac electrophysiology model based on the patient-specific anatomical heart model and electrophysiology measurements of the patient;
means for performing one or more virtual electrophysiological interventions using the patient-specific cardiac electrophysiology model;
means for displaying one or more pacing targets or ablation targets based on the one or more virtual electrophysiological interventions; and
means for updating the patient-specific cardiac electrophysiology model based on results of the electrophysiological intervention.

38. The apparatus of claim 37, wherein the means for updating the patient-specific cardiac electrophysiology model based on results of the electrophysiological intervention comprises:
means for updating the patient-specific cardiac electrophysiology model based on results of an ablation performed in the electrophysiological intervention.

39. The apparatus of claim 38, wherein the means for updating the patient-specific cardiac electrophysiology model based on results of an ablation performed in the electrophysiological intervention comprises:
means for quantifying an ablated region of the patient's heart resulting from the ablation performed in the electrophysiological intervention;
means for updating the patient-specific anatomical heart model to include the ablated region in the patient-specific anatomical heart model; and
means for updating the patient-specific cardiac electrophysiology model based on the updated patient-specific anatomical heart model.

40. The apparatus of claim 39, wherein the means for quantifying an ablated region of the patient's heart resulting from the ablation performed in the electrophysiological intervention comprises:
means for segmenting a necrosis region in an interventional image acquired during the electrophysiological intervention.

41. The apparatus of claim 40, further comprising:
means for personalizing a computational model of heat transfer and cellular necrosis for the patient based on a difference between the segmented necrosis region in the interventional image and a simulated necrosis region computed using the model of heat transfer and cellular necrosis.

42. The apparatus of claim 39, wherein the means for quantifying an ablated region of the patient's heart resulting from the ablation performed in the electrophysiological intervention comprises:
means for computing a necrosis region based on parameters of the ablation performed in the electrophysiological intervention using a patient-specific model of heat transfer and cellular necrosis personalized for the patient based on results of a previous ablation performed in the electrophysiological intervention.

43. The apparatus of claim 37, wherein the means for generating a patient-specific anatomical heart model from medical image data of a patient comprises:
  means for extracting a multi-component patient-specific heart morphology model from the medical image data and fusing the multi-component patient-specific heart morphology model into a single heart model;
  means for segmenting at least one of scar or border zone tissue in the medical image data mapping the segmented at least one of scar or border zone tissue to the single heart model; and
  means for generating a model of myocardium fiber architecture based on the single heart model.

44. The apparatus of claim 37, wherein the means for generating a patient-specific cardiac electrophysiology model based on the patient-specific anatomical heart model and electrophysiology measurements of the patient comprises:
  means for registering the electrophysiology measurements of the patient to the patient-specific anatomical heart model;
  means for estimating patient-specific parameters for the patient-specific cardiac electrophysiology model based on the registered electrophysiology measurements of the patient.

45. The apparatus of claim 37, wherein the electrophysiology measurements of the patient include at least one of invasive cardiac electrophysiology mappings, ECG measurements, or body surface mappings (BSM).

46. The apparatus of claim 37, wherein the means for generating a patient-specific cardiac electrophysiology model based on the patient-specific anatomical heart model and electrophysiology measurements of the patient comprises:
  means for simulating cardiac electrophysiology in the patient-specific anatomical heart model using a computational cardiac electrophysiology model; and
  means for estimating patient-specific parameters of the cardiac electrophysiology model to reduce an error between the simulated cardiac electrophysiology and the electrophysiology measurements of the patient.

47. The apparatus of claim 46, wherein the means for generating a patient-specific cardiac electrophysiology model based on the patient-specific anatomical heart model and electrophysiology measurements of the patient comprises:
  means for estimating patient-specific electrical diffusivity and action potential duration parameters of the patient-specific cardiac electrophysiology model based on the patient-specific anatomical heart model and the electrophysiology measurements of the patient.

48. The apparatus of claim 37, wherein the means for generating a patient-specific cardiac electrophysiology model based on the patient-specific anatomical heart model and electrophysiology measurements of the patient comprises:
  means for estimating patient-specific parameters of the patient-specific cardiac electrophysiology model based on the electrophysiology measurements of the patient using a trained regression function.

49. The apparatus of claim 37, wherein the means for generating a patient-specific cardiac electrophysiology model based on the patient-specific anatomical heart model and electrophysiology measurements of the patient comprises:
  means for estimating patient-specific parameters of the patient-specific cardiac electrophysiology model and adjusting a location and size of at least one of scar or border zone tissue in the patient-specific anatomical heart model based on the electrophysiology measurements of the patient.

50. The apparatus of claim 37, wherein the means for performing one or more virtual electrophysiological interventions using the patient-specific cardiac electrophysiology model comprises:
  means for performing virtual pacing at a plurality of pacing locations and pacing protocols to determine a target pacing location and pacing protocol that induces a cardiac arrhythmia; and
  means for performing virtual ablation at a plurality of ablation locations and ablation protocols to determine a target ablation location and ablation protocol that treats the cardiac arrhythmia.

51. The apparatus of claim 37, wherein the means for performing one or more virtual electrophysiological interventions using the patient-specific cardiac electrophysiology model comprises:
  means for performing virtual pacing at a plurality of pacing locations and pacing protocols to determine target pacing locations and pacing protocols for a cardiac resynchronization therapy.

52. The apparatus of claim 37, wherein the patient-specific cardiac electrophysiology model is a patient-specific cardiac electromechanics model.

53. A non-transitory computer readable medium storing computer program instructions for patient-specific guidance of an electrophysiological intervention, the computer program instructions defining operations comprising:
  generating a patient-specific anatomical heart model from medical image data of a patient;
  generating a patient-specific cardiac electrophysiology model based on the patient-specific anatomical heart model and electrophysiology measurements of the patient;
  performing one or more virtual electrophysiological interventions using the patient-specific cardiac electrophysiology model;
  displaying one or more pacing targets or ablation targets based on the one or more virtual electrophysiological interventions; and
  updating the patient-specific cardiac electrophysiology model based on results of the electrophysiological intervention.

54. The non-transitory computer readable medium of claim 53, wherein updating the patient-specific cardiac electrophysiology model based on results of the electrophysiological intervention comprises:
  updating the patient-specific cardiac electrophysiology model based on results of an ablation performed in the electrophysiological intervention.

55. The non-transitory computer readable medium of claim 54, wherein updating the patient-specific cardiac electrophysiology model based on results of an ablation performed in the electrophysiological intervention comprises:
  quantifying an ablated region of the patient's heart resulting from the ablation performed in the electrophysiological intervention;
  updating the patient-specific anatomical heart model to include the ablated region in the patient-specific anatomical heart model; and
  updating the patient-specific cardiac electrophysiology model based on the updated patient-specific anatomical heart model.

56. The non-transitory computer readable medium of claim 55, wherein quantifying an ablated region of the patient's heart resulting from the ablation performed in the electrophysiological intervention comprises:
  segmenting a necrosis region in an interventional image acquired during the electrophysiological intervention.

57. The non-transitory computer readable medium of claim 56, wherein the operations further comprise:
  personalizing a computational model of heat transfer and cellular necrosis for the patient based on a difference between the segmented necrosis region in the interventional image and a simulated necrosis region computed using the model of heat transfer and cellular necrosis.

58. The non-transitory computer readable medium of claim 55, wherein quantifying an ablated region of the patient's heart resulting from the ablation performed in the electrophysiological intervention comprises:
  computing a necrosis region based on parameters of the ablation performed in the electrophysiological intervention using a patient-specific model of heat transfer and cellular necrosis personalized for the patient based on results of a previous ablation performed in the electrophysiological intervention.

59. The non-transitory computer readable medium of claim 53, wherein generating a patient-specific anatomical heart model from medical image data of a patient comprises:
  extracting a multi-component patient-specific heart morphology model from the medical image data and fusing the multi-component patient-specific heart morphology model into a single heart model;
  segmenting at least one of scar or border zone tissue in the medical image data mapping the segmented at least one of scar or border zone tissue to the single heart model; and
  generating a model of myocardium fiber architecture based on the single heart model.

60. The non-transitory computer readable medium of claim 53, wherein generating a patient-specific cardiac electrophysiology model based on the patient-specific anatomical heart model and electrophysiology measurements of the patient comprises:
  registering the electrophysiology measurements of the patient to the patient-specific anatomical heart model;
  estimating patient-specific parameters for the patient-specific cardiac electrophysiology model based on the registered electrophysiology measurements of the patient.

61. The non-transitory computer readable medium of claim 53, wherein the electrophysiology measurements of the patient include at least one of invasive cardiac electrophysiology mappings, ECG measurements, or body surface mappings (BSM).

62. The non-transitory computer readable medium of claim 53, wherein generating a patient-specific cardiac electrophysiology model based on the patient-specific anatomical heart model and electrophysiology measurements of the patient comprises:
  estimating patient-specific electrical diffusivity and action potential duration parameters of the patient-specific cardiac electrophysiology model based on the patient-specific anatomical heart model and the electrophysiology measurements of the patient.

63. The non-transitory computer readable medium of claim 53, wherein generating a patient-specific cardiac electrophysiology model based on the patient-specific anatomical heart model and electrophysiology measurements of the patient comprises:
  simulating cardiac electrophysiology in the patient-specific anatomical heart model using a computational cardiac electrophysiology model; and
  estimating patient-specific parameters of the cardiac electrophysiology model to reduce an error between the simulated cardiac electrophysiology and the electrophysiology measurements of the patient.

64. The non-transitory computer readable medium of claim 53, wherein generating a patient-specific cardiac electrophysiology model based on the patient-specific anatomical heart model and electrophysiology measurements of the patient comprises:
  estimating patient-specific parameters of the patient-specific cardiac electrophysiology model based on the electrophysiology measurements of the patient using a trained regression function.

65. The non-transitory computer readable medium of claim 53, wherein generating a patient-specific cardiac electrophysiology model based on the patient-specific anatomical heart model and electrophysiology measurements of the patient comprises:
  estimating patient-specific parameters of the patient-specific cardiac electrophysiology model and adjusting a location and size of at least one of scar or border zone tissue in the patient-specific anatomical heart model based on the electrophysiology measurements of the patient.

66. The non-transitory computer readable medium of claim 53, wherein performing one or more virtual electrophysiological interventions using the patient-specific cardiac electrophysiology model comprises:
  performing virtual pacing at a plurality of pacing locations and pacing protocols to determine a target pacing location and pacing protocol that induces a cardiac arrhythmia; and
  performing virtual ablation at a plurality of ablation locations and ablation protocols to determine a target ablation location and ablation protocol that treats the cardiac arrhythmia.

67. The non-transitory computer readable medium of claim 53, wherein performing one or more virtual electrophysiological interventions using the patient-specific cardiac electrophysiology model comprises:
  performing virtual pacing at a plurality of pacing locations and pacing protocols to determine target pacing locations and pacing protocols for a cardiac resynchronization therapy.

68. The non-transitory computer readable medium of claim 53, wherein displaying one or more pacing targets or ablation targets based on the one or more virtual electrophysiological interventions comprises:
  displaying the one or more pacing targets or ablation targets on a visualization of the patient-specific anatomical heart model.

69. The non-transitory computer readable medium of claim 53, wherein displaying one or more pacing targets or ablation targets based on the one or more virtual electrophysiological interventions comprises:
  displaying the one or more pacing targets or ablation targets on an interventional image acquired during the electrophysiological intervention.

70. The non-transitory computer readable medium of claim 53, wherein the patient-specific cardiac electrophysiology model is a patient-specific cardiac electromechanics model.

* * * * *